United States Patent
Ryan

(10) Patent No.: US 10,262,112 B2
(45) Date of Patent: Apr. 16, 2019

(54) PRESCRIPTION DECISION SUPPORT SYSTEM AND METHOD USING COMPREHENSIVE MULTIPLEX DRUG MONITORING

(71) Applicant: Sano Informed Prescribing Inc, Franklin, TN (US)

(72) Inventor: Timothy P. Ryan, Franklin, TN (US)

(73) Assignee: Precera Bioscience, Inc., Franklin, TN (US)

( * ) Notice: Subject to any disclaimer, the term of this patent is extended or adjusted under 35 U.S.C. 154(b) by 857 days.

(21) Appl. No.: 14/827,036

(22) Filed: Aug. 14, 2015

(65) Prior Publication Data

US 2015/0371003 A1 Dec. 24, 2015

Related U.S. Application Data

(63) Continuation-in-part of application No. 14/171,955, filed on Feb. 4, 2014, now abandoned.
(Continued)

(51) Int. Cl.
*G16H 20/10* (2018.01)
*G06F 19/00* (2018.01)
(Continued)

(52) U.S. Cl.
CPC ......... *G06F 19/3456* (2013.01); *G06Q 10/10* (2013.01); *G06Q 50/22* (2013.01)

(58) Field of Classification Search
CPC ..... G06F 19/3456; G06F 19/00; G06Q 10/10; G06Q 50/22; G16H 10/30; G16H 20/10
See application file for complete search history.

(56) References Cited

U.S. PATENT DOCUMENTS 5,642,731 A * 7/1997 Kehr ............... A61J 7/0481
600/300
2003/0211636 A1 11/2003 Bedian et al.
(Continued)

FOREIGN PATENT DOCUMENTS

KR 20090033837 4/2009
WO 200206826 1/2002
(Continued)

OTHER PUBLICATIONS

Johannes H Proost, Dirk KF Meijer, MW/Parm, an integrated software package for drug dosage regimen calculation and therapeutic drug monitoring. Computers in Biology and Medicine May 1992, vol. 22, Issue 3, p. 155-163 (Year: 1992).*
(Continued)

*Primary Examiner* — Victoria P Augustine
*Assistant Examiner* — Chad A Newton
(74) *Attorney, Agent, or Firm* — Patterson Intellectual Property Law, P.C.; Gary L. Montle

(57) ABSTRACT

A decision support system and method for optimizing medication dosages includes comprehensive patient databases correlating medications and exposure values across data models having pharmacokinetic and pharmacodynamic dimensions. The system determines distinctions between expected and detected medications and exposure values for a patient, and further distinguishes between non-compliant patients from compliant patients having high metabolizing characteristics with respect to certain expected but undetected medications. The system links to and reconciles the patient medical record accordingly. Graphical user interfaces display recommended dosages and projected exposure ranges for the expected and detected medications. In an embodiment, the interface presents certain alternative treatment options determined as being available with respect to
(Continued)

the expected but undetected medications. The user in an embodiment may manipulate or select respective nominal dosage values or alternative treatment options, wherein projected exposure values are dynamically calculated and displayed for each of the medications.

15 Claims, 10 Drawing Sheets

Related U.S. Application Data

(60) Provisional application No. 61/760,193, filed on Feb. 4, 2013.

(51) Int. Cl.
*G06Q 10/10* (2012.01)
*G06Q 50/22* (2018.01)

(56) References Cited

U.S. PATENT DOCUMENTS

| | | | |
|---|---|---|---|
| 2007/0203751 A1* | 8/2007 | Koblasz | G16H 10/65 705/2 |
| 2009/0076338 A1 | 3/2009 | Zdeblick et al. | |
| 2009/0171697 A1 | 7/2009 | Glauser et al. | |
| 2010/0039378 A1* | 2/2010 | Yabe | G06F 3/017 345/156 |
| 2010/0121170 A1 | 5/2010 | Rule | |
| 2011/0294194 A1* | 12/2011 | Gottwein | C07K 14/005 435/235.1 |
| 2012/0041778 A1 | 2/2012 | Kraft | |
| 2012/0136583 A1* | 5/2012 | Lazar | G06F 19/18 702/19 |
| 2012/0232045 A1 | 9/2012 | Goren et al. | |
| 2012/0238030 A1 | 9/2012 | Rappold et al. | |
| 2012/0316897 A1 | 12/2012 | Hanina et al. | |
| 2012/0323141 A1 | 12/2012 | Maier et al. | |
| 2013/0209565 A1* | 8/2013 | Hedner | A61K 9/2054 424/490 |

FOREIGN PATENT DOCUMENTS

| | | |
|---|---|---|
| WO | 2005041105 | 5/2005 |
| WO | 2008043724 | 4/2008 |

OTHER PUBLICATIONS

Theodoridis et al. Liquid chromatography-mass spectrometry based global metabolite profiling: A review. Analytica Chimica Acta vol. 711, pp. 7-16 (Year: 2012).

Johannes H. Proost, Dirk KF Meijer. MS/Pharm, an integrated software package for drug dosage regimen calculation and therapeutic drug monitoring. Computers in Biology and Medicine. May 1992, vol. 22, Issue 3, pp. 155-163 (Year: 1992).

Assaf Gottlieb, Gideon Y Stein, Yoram Oron, Eytan Ruppin, Roded Sharan. INDI: a computational framework for inferring drug interactions and their associated recommendations. Jul. 2012, Molecular Systems Biology 8:592, pp. 1-12 (Year: 2012).

Ansermot et al. Simultaneous quantification of selective serotonin reuptake inhibitors and metabolites in human plasma by liquid chromatography-electrospray mass spectrometry for therapeutic drug monitoring. Journal of chromatography B, 2012, 885-886, pp. 117-130.

E. Haen. Therapeutic Drug Monitoring in Pharamacovigilance and Pharmacotherapy Safety. Pharmacopsychiatry 2011; 44(06); pp. 254-258.

Thakrar et al. Detecting signals of drug-drug interactions in a spontaneous reports database. Br J Clin Pharmacol, 64:4, pp. 489-49.

You et al. A Drug Administration Decision Support System. 2012 IEEE Conference on Bioinformatics and Biomedicine Workshops, Oct. 2012, pp. 122-129.

U Chiuminatto, F Gosetti, P Dossetto, E Maxxucco, D Zampieri, E. Robotti, MC Gennaro, E Marengo, Automated Online Solid Phase Extraction Ultra High Performance Liquid Chromatography Method Coupled with Tandem Mass Spec for Determination of Forty-Two Therapeutic Drugs and Drugs of Abuse in Human Urine. anal Chem 2010, vol. 82, No. 13, p. 5636-5645.

\* cited by examiner

PRESCRIPTION DECISION SUPPORT SYSTEM AND METHOD USING COMPREHENSIVE MULTIPLEX DRUG MONITORING

CROSS-REFERENCES TO RELATED APPLICATIONS

This application is a continuation-in-part of co-pending U.S. patent application Ser. No. 14/171,955, filed Feb. 4, 2014, which further claims benefit of U.S. Provisional Patent Application No. 61/760,193, filed Feb. 4, 2013. The aforementioned disclosures are incorporated herein by reference in their entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The present invention relates generally to drug prescription practices for healthcare providers. More particularly, this invention relates to a system and method for diagnostic monitoring of drug and biomarker levels, relating these measured levels to other patient-specific characteristics, and utilizing this real-time and measurement-based drug level data for optimizing medication choice and dosages for patients taking more than one medication.

Therapeutic Drug Monitoring (TDM) is a term that describes the measurement of drug exposure in, e.g., serum or plasma to tailor dosing in an individual patient. Tailored dosing in individuals is necessary because a multitude of parameters, such as body weight, overall health, patient behavior, and genotype underlie variable drug exposure in patients administered the same dose of a given medication. Different exposures result in different outcomes. For some drugs, such as the blood thinner Warfarin™, TDM is routine, with the physician starting, on a patient by patient basis, with very low doses and slowly titrating to efficacious blood levels to avoid potentially fatal bleeding.

TDM is not routinely practiced with most medications, not because exposure is any less dependent on individual patient parameters, but because it is not deemed necessary when the margin between efficacy and toxicity is wide. Therefore, TDM is typically deployed to avoid toxicity rather than to maximize the effectiveness of individual drugs.

Drug exposure is not only dependent upon the physical makeup of individual patients, but also upon interactions with other drugs that are concomitantly administered. Drug-drug interactions (DDI's) have a substantial impact upon patient outcomes, even with very commonly administered medications. Simvastatin™, for example, is one of the world's most prescribed medications. Co-administration of drugs that inhibit metabolic enzymes and transporters, such as cyclosporine, can drive Simvastatin™ exposure in individual patients upward more than ten-fold, increasing incidence of rhabdomyolysis, a serious and sometimes fatal toxicity of the muscle. This type of interaction is common, and nearly all new medications brought to market carry with them some interaction potential as either a perpetrator or victim of drug-drug interactions despite the best efforts of the pharmaceutical industry ("pharma").

One key point which is worth considering is that nominal therapeutic ranges of Simvastatin™ and virtually all other drugs are known or at least predetermined. Exposure and identification of medications outside of their range may be easily monitored by measuring drug levels in blood, but measuring drug exposure, especially the exposure of multiple drugs in unison, is not standard practice today. Assays that combine the measurement of drugs and biomarkers in multiplex format to decrease diagnostic costs while streamlining prescribing practices are further not previously implemented in the art.

The influence of genetics, patient characteristics and behaviors, environment, and drug-drug interactions on patient outcomes have all been studied on an individual basis, but currently have little impact on physician prescribing habits. Currently, a physician cannot account for the inherent complexity these parameters impart when prescribing a new medication to a patient, especially given that patients over 65 years of age are often taking 8 or more medications simultaneously. In fact, prospectively building models that predict drug exposure in an individual patient's overall treatment regimen to help guide physicians in drug selecting and dosing would require a comprehensive data set that simply does not exist today. Drug exposure in the light of complexity must be quantified if we are to understand drivers of patient variability.

Therefore, what is needed is a system and/or method for measuring the exposure of all concomitant medications in individual patients and a means to apply this information to inform physician prescribing practices. Such systems and methods may desirably serve one or more purposes including but not limited to: providing a real-world diagnostic monitoring; enabling better prescribing practices resulting in reduced risk for patients; yielding more effective treatment outcomes by increasing compliance, decreasing hospitalizations and optimizing medication choice; streamlining costs by integrating biomarker and therapeutic drug monitoring assays; producing valuable data necessary for prospective modeling of patient characteristics and reporting measures for better drug development in the future; and yielding critical insights on the benefit-risk and the real world effectiveness of pharmaceutical products for regulators, payers, HTA agencies, pharma and ultimately, patients.

It would be desirable that such systems and methods produce results easily for presentation to the physician in a simple format such that prescribing practices can be optimized for each patient in, e.g., a fifteen minute consultation.

Therefore, it would further be desirable to restrict the amount and scope of information provided, and to present this information in a graphical format with clear recommendations.

It is still further desirable that empirical tools implemented by a system and method as disclosed herein demonstrate where medical records for patients are wrong (e.g., they do not inform multiple physicians of medications that the patient is actually taking), compliance is poor (e.g., where patients are not taking medications prescribed to them), and medication duplicity is common (e.g., multiple medications of the same class are co-prescribed).

BRIEF SUMMARY OF THE INVENTION

In accordance with various embodiments and associated aspects of the present invention, systems and methods as described herein are implemented for understanding patient variability in drug response resulting in the refinement of current prescribing practices and leveraging recent advances in mass spectrometry and informatics. A universal drug monitoring diagnostic tool is provided and executed for producing a simplified, comprehensive report that allows physicians to make informed prescription decisions in real time with individual patients.

Underlying this report are complexities that drive patient variability that are taken into account and presented to the physician in the form of drug selection and dosing recommendations. These constantly evolving/improving data-driven recommendations informed prescribing more so than current alert systems, which are overwhelmingly overridden in current practice today.

In one aspect of a system and method of the present disclosure, this diagnostic tool and associated implementation methods (which may in certain embodiments described further herein be referred to herein as "Comprehensive Informed Prescribing" or "CIP") is a solution that leverages exposure of multiple medications and biomarkers simultaneously, allowing data-driven prescribing decisions based on individual drug levels in the context of for example other drugs, patient characteristics and reporting measures.

In another aspect, systems and methods as disclosed herein factor underlying patient, environmental and drug-driven variability and puts them in the hands of the physician in an easy to administer format.

In another aspect, systems and methods as disclosed herein may measure multiple (e.g., >100) chemical entities in a multiplex format for the purpose of providing quantitative data for informed dosing. The multiplex assay of drugs and metabolites may be designed using co-prescribing frequency, pharmacokinetic, pharmacodynamics, and pharmacogenomics principals, defined so as to cover a sizable majority of written prescriptions (e.g., ~95% of small molecule scripts). Chemical entities include not just single victim drugs that fit the criteria for single drug monitoring, but perpetrator drugs that interact with victim drugs and drive DDIs. Further, endogenous biomarkers, non-prescription drugs, specified food additives, and natural products may be included in measurement.

In another aspect, the medications in this multiplex assay may be coded by therapeutic class, chemical structure, metabolic routs of elimination, and genetic determinants of metabolism relative to each patient.

In another aspect, output data from the multiplex assay may be used for each patient to produce an accurate account of medications being taken by the patient in the form of a patient medication profile. This profile may be used to reconcile the health record of the patient, primarily when medications are detected in body fluids of the patient that are not in the medical record at time of dosing. The new information may be used to update the primary medical record through either manual or automated reconciliation.

In another aspect, output data from the multiplex assay may be used for each patient to produce a snapshot of patient compliance when medications are in the primary health record, but not detected in patient body fluids. This information may be utilized to update the primary medical record through either manual or automated reconciliation. For example, if both patent drug and metabolic breakdown products are not detected, and the pharmacokinetics determine that they should be detectable using known pharmacokintetic properties, non-compliance would be suspected. Alternatively, if only the parent drug or select metabolites are detected outside of known pharmacokinetic properties, inherent patient variability, such as genetic polymorphism presence, would be suspect, triggering a variety of diagnostic or treatment options.

In another aspect, output data from the multiplex assay may be analyzed relative to therapeutic class to illustrate non-intentional polypharmacy redundancy in treatment, which is common and increases proportionally to the number of prescribing physicians.

In another aspect, systems and methods according to the present disclosure may implement algorithms associating multiplex drug measurement data with patient meta-data and outcome data, models derived from these associations, and any novel recommendations that impact drug administration resulting from initial multiplex drug measurement. Associations may be made with non-traditional data, such as patient characteristics and behaviors, genetic makeup, disease state, and measured compliance.

In another aspect, systems and methods according to the present disclosure may generate an informed prescribing report that allows physicians to make point-of-care decisions based on graphical output depicting each chemical entity detected, the measured value of that entity, the value of that entity relative to targeted therapeutic range, and recommendations based on the output from a contextual effectiveness database.

In another aspect, systems and methods according to the present disclosure may implement a comprehensive exposure/outcome database, models derived therein, and novel drug-drug and drug-chemical interactions detected using these models. The application of these models may extend back to drug development in the form of alerts for avoidable DDIs and previously unidentified avenues of unmet patient need. Empirical data within the relational database can be used to re-define the therapeutic range of individual drugs when sufficient data are accumulated to be deemed superior to existing range estimates.

In another aspect, systems and methods according to the present disclosure may implement multiplex drug measurement in streamlining assay cost, physician decision making, maintaining of patient health, improving compliance and overall efficacy, and preventing adverse events.

In another aspect, systems and methods according to the present disclosure measure all marketed drugs and produce an output of only relevant information that identifies information such as for example: which drugs the patient is taking (compliance); the level of each drug relative to the desired therapeutic range; and treatment options for each drug (including drug switching) when the level is either too high, too low, or subject to interactions leveraging context of the CIP database.

In another aspect, systems and methods according to the present disclosure generate and provide an output to a physician or other healthcare provider, having sufficient data and clear recommendations to treat the patient with autonomy. In various embodiments, additional parameters may include for example co-measurement of key select biomarkers, non-prescription medications and other influencing factors.

DEFINITIONS

Figure 1:
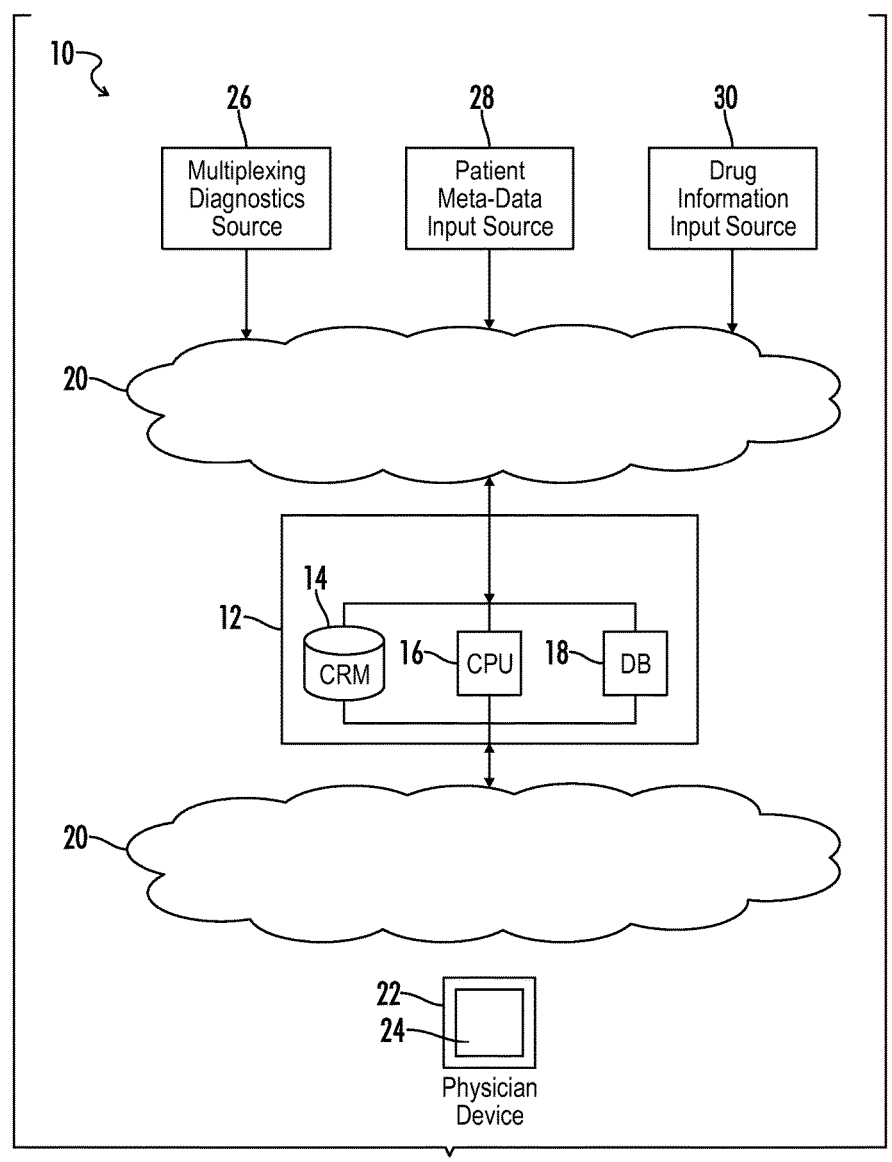
FIG. 1 is a block diagram representing an exemplary embodiment of a system of the present disclosure.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "Drug-drug interactions (DDIs)" as used herein may refer to at least interactions whereby one chemical entity has been demonstrated to or by inferences is expected to alter the level, efficacy, safety, or effectiveness of a prescribed medication when administered together.

The term "efficacy" as used herein may refer to at least the capacity to produce a desired clinical effect in a treated population relative to a population not treated with test drug. The desired effect may typically be measured based upon statistically significant patient cohort differences.

The term "effectiveness" as used herein may refer to at least some form of tangible, real world evidence as would be understood by those of skill in the art to demonstrate that an administered drug produces desired outcomes in individual patients.

The term "comprehensive informed prescribing" as used herein may refer to at least a process from initial patient consultation through outcome-driven patient care that utilizes multiplex drug measurement and associated tools allowing the physician to make data-driven decisions at the patient level in drug selection, prescribing changes, and dosage adjustments.

The term "multiplex drug measurement" as used herein may refer to at least the measure of more than one chemical entity using a single collection and assay format.

The term "perpetrator" as used herein may refer to at least a chemical entity that causes interference with a drug.

The term "personal comprehensive drug compendium" or "PCDC" may refer to at least a composition of all prescribed and non-prescribed medications that each individual patient is taking at time of physician visit.

The term "polypharmacy" as used herein may refer to at a prescribing practice where one patient is prescribed more than one concomitant medication.

The term "therapeutic range" as used herein may refer to at least a calculated or otherwise derived concentration range where efficacy has been demonstrated and toxicological side effects are avoided.

The term "victim drug" as used herein may refer to at least a drug whose levels are affected by perpetrators.

The term "Medical Therapy Management" or "MTM" as used herein may refer to at least a distinct service or group of services that optimizes drug therapy with the intent of improved therapeutic outcomes for individual patients. This model focuses on alerting drug interactions derived from a formulary or statistical approach.

The term "compliance" or "compliant" as used herein may refer to at least a state wherein a patient is determined to have taken expected or prescribed medications, further in a dosage as expected or otherwise as prescribed by a healthcare provider and typically in accordance with the relevant medical record.

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

The term "communications network" as used herein with respect to data communication between two or more parties or otherwise between communications network interfaces associated with two or more parties may refer to any one of, or a combination of any two or more of, telecommunications networks (whether wired, wireless, cellular or the like), a global network such as the Internet, local networks, network links, Internet Service Providers (ISP's), and intermediate communication interfaces.

DETAILED DESCRIPTION OF THE INVENTION

In various embodiments as disclosed herein, and by reference first to FIG. 1, a comprehensive informed prescribing system 10 may include one or more servers 12 upon which reside a processor 16, databases 18 and one or more computer-readable memory media 14. The memory media 14 have program instructions residing thereon which upon execution by the processor 16 are effective to direct the performance of steps collectively associated with methods of the present invention.

The system 10 may include or otherwise integrate or coordinate with an individual computing device 22 associated with a particular healthcare provider which is programmed to execute some or all steps of the method, and further effective to communicate via a communications network 20 and in distributed fashion with remote servers, databases 28, 30, multiplex assay systems 26 or the like for the purpose of facilitating certain steps of the method.

Alternatively, a central server may include components for performing most or all of the steps of an exemplary method in association with computers associated with the healthcare provider. For example, the steps in an exemplary method may be directed by program modules residing on a central server, based on requests or commands provided remotely from a healthcare provider using a mobile computing device, and further effective to generate a user interface such as for example a website accessible via a communications network to receive or provide data to and from the healthcare provider.

Systems and methods as disclosed herein may accordingly produce a single diagnostic that measures multiple biomarkers, marketed drugs and their active metabolites, giving the prescriber an unprecedented look into drug exposure that automatically takes into account heterogeneity of treatment for each patient. Furthermore, with reference to FIG. 4 by way of example, a simplified output could be formatted into a chart 40 from which dose and prescription decisions can be made and changed over time. With this diagnostic in hand, the prescriber has endpoint information directly influenced by genetics, physiology, DDIs, pharmaceutical compliance, all other covariates that effect drug exposure.

Figure 2:
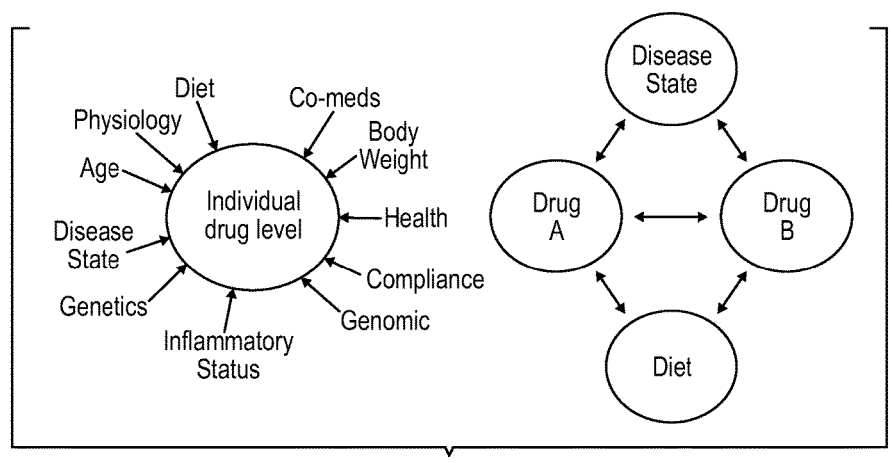
FIG. 2 is a graphical representation of exemplary parameters as may be influencing individual drug levels with respect to a drug level monitoring process of the present disclosure.

Furthermore, with this information, the prescriber would be able to determine which drugs are in the therapeutic range and hence, how to change dosing not for one, but every drug the patient is taking without bias and influence from doctor patient interactions. This is illustrated by way of example in FIG. 2.

It is conceived that a system and method as disclosed herein be provided to or accessible by physicians for leveraging the prescription network, databases, and informatics algorithms already developed within the industry. For example, the system may integrate or otherwise communicate with one or more remote servers and/or databases (collectively labeled as 30) for the purpose of obtaining, extracting or collecting data, requesting third-party execution of processing engines for the purpose of generating a desired analytics output, etc.

Figure 3:
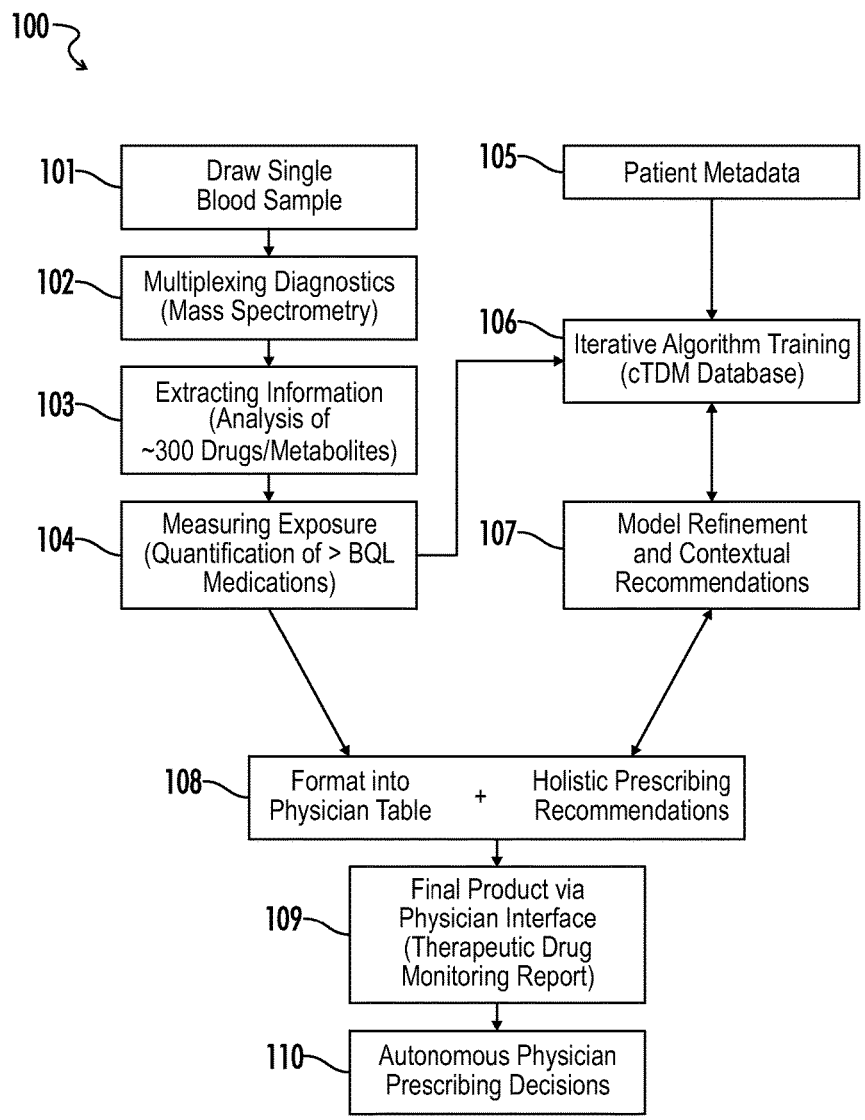
FIG. 3 is a flowchart representing an exemplary process of the present disclosure.

By reference next to FIG. 3, an exemplary embodiment of a method 100 according to the present invention may be performed as follows. The steps of the method may generally be performed in the order described, but such order is not necessarily limiting on the scope of the invention unless otherwise stated or inherently required. The described steps are not intended as being comprehensive in nature, and additional steps or sub-steps may be desirable for performing the method or otherwise achieving the purposes associated with the present invention, as may be understood by those of skill in the art.

As a preliminary matter, a patient profile may be generated in association with a particular patient (step 105). Accordingly, patient data may be gathered and incorporated into a contextual database data including, but not limited to, patient characteristics and behaviors, genetic makeup, disease state, non-prescription medications, diet, and other parameters known to influence drug levels.

Each of a plurality of chemical entities associated with a patient is measured in a multiplex assay from a single, non-invasive patient collection of body fluid such as, e.g., blood (steps 101, 102). As previously noted, methods to measure multiple drugs (e.g., >100) with different therapeutic indications for the purpose of comprehensive therapeutic range targeting are not widespread if even previously available in the art, making it cost and time prohibitive to monitor individual patient compliance, adjust dosage and choose medications appropriately. In accordance with a system and method of the present disclosure, a plurality of chemical entities including, but not limited to, commonly prescribed medications may be measured in a single assay format.

Generally stated, contemporary drugs are universally developed with an understanding of pharmacokinetic/pharmacodynamic or "PK/PD" principles. Accordingly, the individual molecular structures and estimated reference therapeutic ranges are known upon entry into the marketplace. Measuring drug levels on a single drug is known in the art using a multitude of technologies. The concept of expanding the measurement of a single molecular entity from one blood draw coupled with a single mass spectrometry run to measuring hundreds of molecular entities using the same blood sample via multiplex mass spectrometry is further available due to at least increased resolution in mass spectrometry technology, and deconvolution algorithms that can extract and quantify drug levels from the mass spectrum (step 103).

It is anticipated that demand created using an approach as disclosed herein may desirably result in improved multiplex assay formats being developed for the purpose of comprehensive informed prescribing, and the use of these multiplex assays for informed prescribing may also be considered within the scope of various embodiments of the present invention.

In various embodiments, systems and methods as disclosed herein generally rely upon the measurement of exposure of all drugs in samples of, e.g., whole blood, serum, plasma, etc., to tailor dosing in individual patients taking multiple and simultaneous medications. Tailoring with respect to individuals is provided because a multitude of parameters, such as body weight, overall health, patient behavior, drug interaction, and genotype may typically underlie variable drug exposure in patients administered the same dose of a given medication (step 104). Different exposures result in different outcomes.

Figure 4:
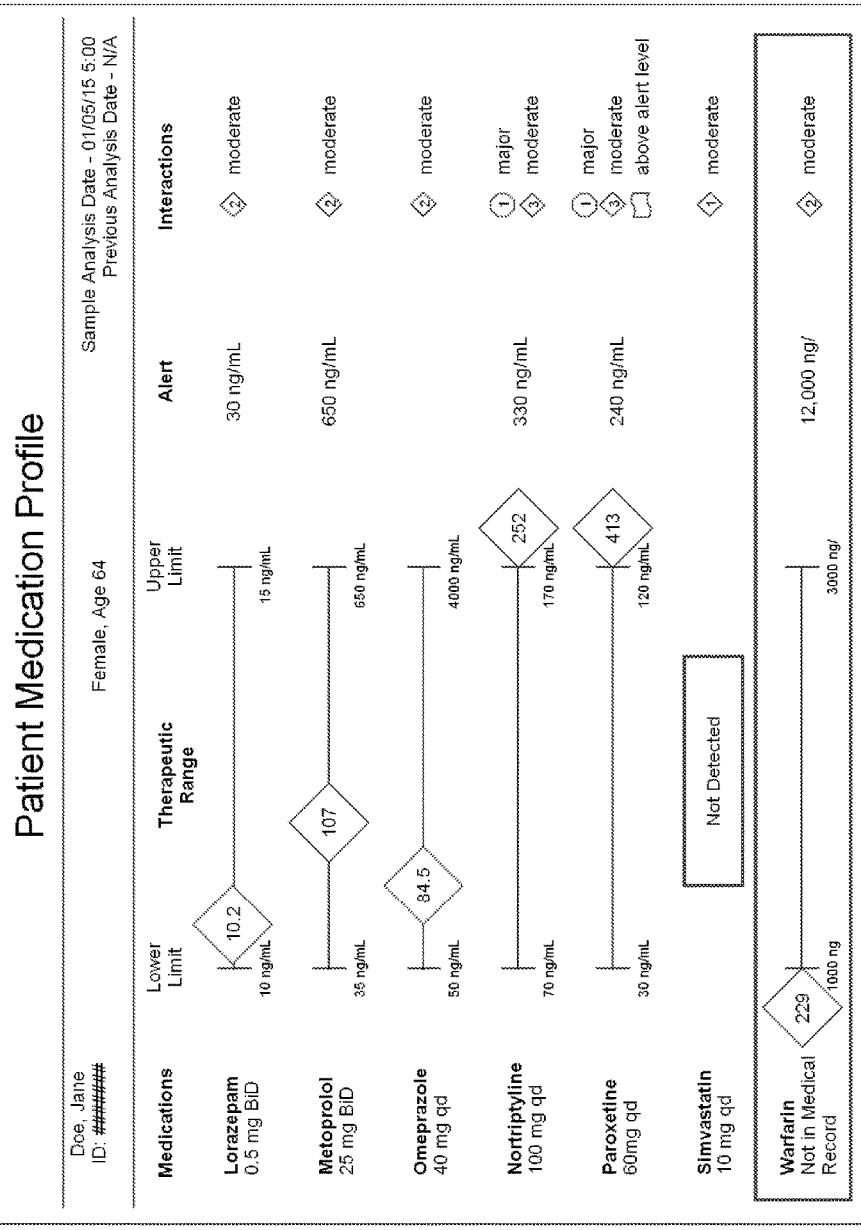
FIG. 4 is a modified screen shot representing an exemplary user interface as a drug level report according to the present disclosure.

Medication levels are identified for each of the plurality of measured chemical entities relative to respective target therapeutic ranges. As represented in FIG. 4, the measurements may be formatted into a physician table along with holistic prescribing recommendations as further described below (step 108) and subsequently highlighted in a report or display associated with a user interface (step 109) with respect to minimum and maximum ends of a target range which is predetermined with respect to the various chemical entities, and obtainable from any of a number of external data sources.

A drug interaction program module is iteratively trained with the identified medication levels and either or both of incoming and historical patient data/parameters from the patient profile (106). The drug interaction program module or engine using appropriate algorithms may be executed to account for drug-drug interactions or the like using models based upon the measurement of multiple concomitant medications in the patient. Current methods for defining drug-drug interactions typically use models derived from in vitro, ex vivo, and small pair-wise clinical trial data. Dosing recommendations and contraindication information are thus limited by these fragmentary input data. In accordance with the present disclosure, iterative training of a proprietary model over time with incoming data may facilitate individual PCDC drug-drug interaction recommendations based upon multiple interacting medications in light of all other parameters measured in effectiveness research. In various embodiments of the present invention, a number of associations may be further made available using the novel data source whereby concomitant drug levels are used as covariates in the derivation of dosing advisement and recommendations.

In various embodiments, a drug choice and dosage recommendation program module may be executed to generate a recommended dosage for each of the plurality of chemical entities based on an output from the drug interaction program module and a determined effectiveness for each of the plurality of chemical entities (step 107). Current best-practice prescribing for individual medications is dosage-based and driven by drug labels that are constructed from controlled clinical trials. These clinical trials measure average efficacy, safety, and biopharmaceutical endpoints in controlled patient populations. The dosage recommendation program module and associated algorithms may alternatively generate data-driven dosing outputs based upon measured individual drug levels targeting therapeutic ranges defined by real-world effectiveness data. Accordingly, individual drug measurement in an accessible body fluid as previously described accounts for all parameters impacting individual patient drug disposition and may be viewed in the context of an effectiveness database.

Further, treatment options for physicians as previously known in the art are primarily formulary driven. There is no tool that informs patient prescribing that can bring data to the physician to allow real-time patient prescribing decisions in patient setting.

Accordingly, and by further reference again to FIG. 4, any one or more of the recommended dosage, the identified medication levels, the target therapeutic ranges, and other desired information may be presented to a user such as a healthcare provider via a graphical user interface which may for example be executable from any of a number of types of mobile computing device associated with the healthcare provider. Please note that the medications and associated values, ranges, flags, interactions and recommendations provided in both of FIGS. 4 and 5 are completely hypothetical and are presented for illustrative purposes only and without limitation.

Alternatively, a report may be generated in electronic form and downloadable by the healthcare provider or otherwise locally printable, or various equivalent delivery modes as may be understood by those of skill in the art.

Figure 5:
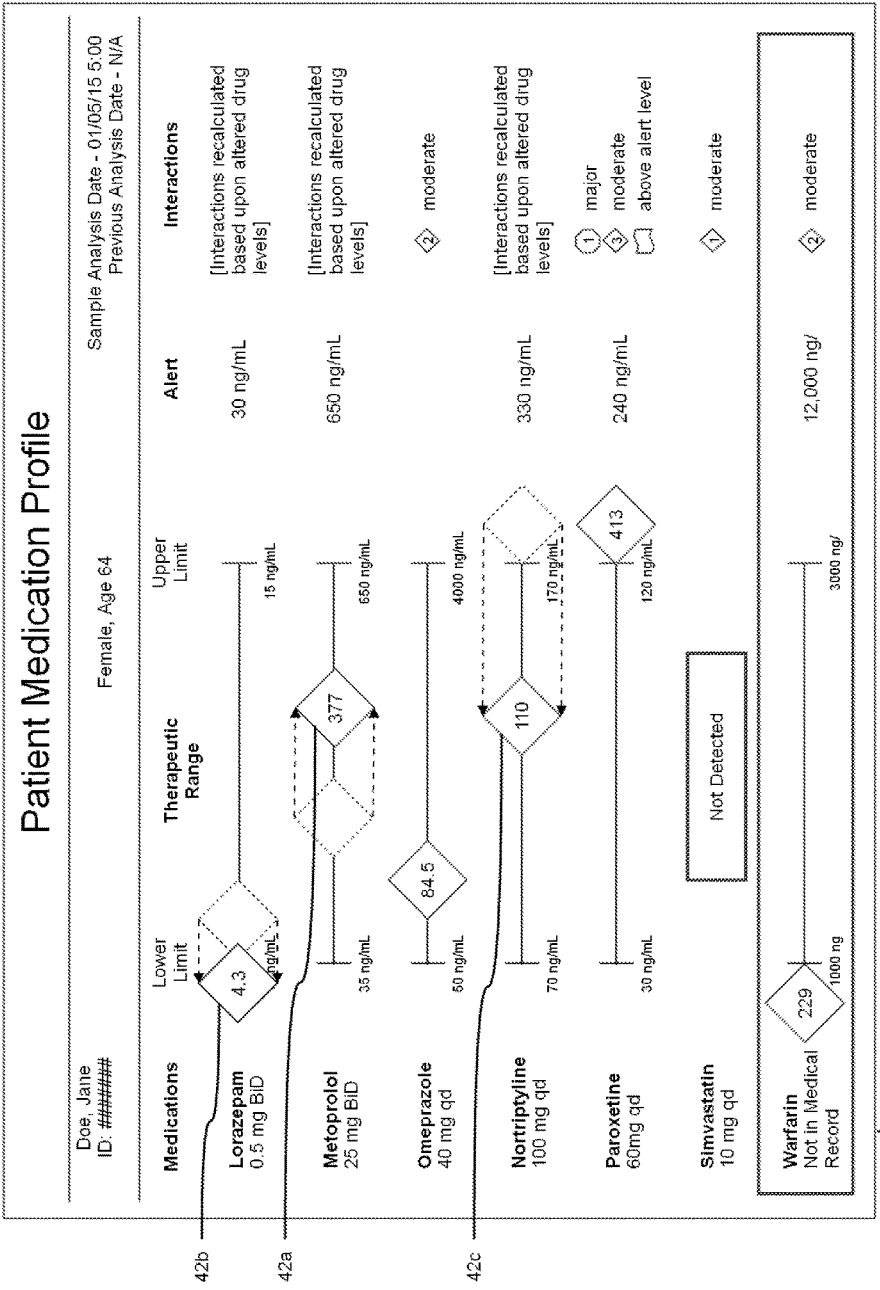
FIG. 5 is a modified screen shot representing an interactive version of the user interface of FIG. 4.

Referring now to FIG. 5, in an embodiment the report may further be generated in an interactive format 40b wherein the user may selectably modify one or more of the measured drug levels. Hosted algorithms associated with the system of the present invention may in various embodiments subsequently recalculate or otherwise determine the various drug-drug interactions, dependencies, target therapeutic ranges, and any other relevant report output as may be influenced by or otherwise relevant to the new user selection. For example, if a user were to select the measured value for Metoprolol (25 mg BiD ng/mL), which selection may be made by for example touching the relevant icon 42a via a touch screen display or otherwise by mouse selection or any of a number of equivalents as are known in the art, and slide the icon 42a to any other value along the represented scale (and even potentially outside of the lower and upper limits), the system may be programmed to reevaluate one or more of the other values, for example those for Lorazepam 42b and/or Nortriptyline 42c as represented in FIG. 5. In this instance, if the user were to select a higher value of Olanzapine, the system may further revise the flag level, revise the target level or otherwise provide comments with respect to for example Lithium, as there are known contraindications with respect to these two medications.

A graphical user interface such as a touch screen dashboard display in accordance with various embodiments of the present invention may therefore be implemented for the purpose of establishing base data for a patient profile or to receive input parameters for one or more associated algorithms, and further may after initial presentation of output values allow for user manipulation of one or more output values to resubmit some or all of the results for recalculation, reevaluation and subsequent presentation of alternative results. A physician may therefore monitor potential courses of action in real-time based on suggested dosing or drug selection, rather than relying solely on future results from current doing and drug selection.

It may be understood by those of skill in the art that results may be fed over time into system processing engines such as for example neural network, or machine learning, engines that implement advanced algorithms for improving upon the associations, interactions, recommendations and other results with respect to initial iterations of the process. Particularized informational databases and associated program modules may be provided within the scope of the present invention for operating on the relevant data.

Figure 6:
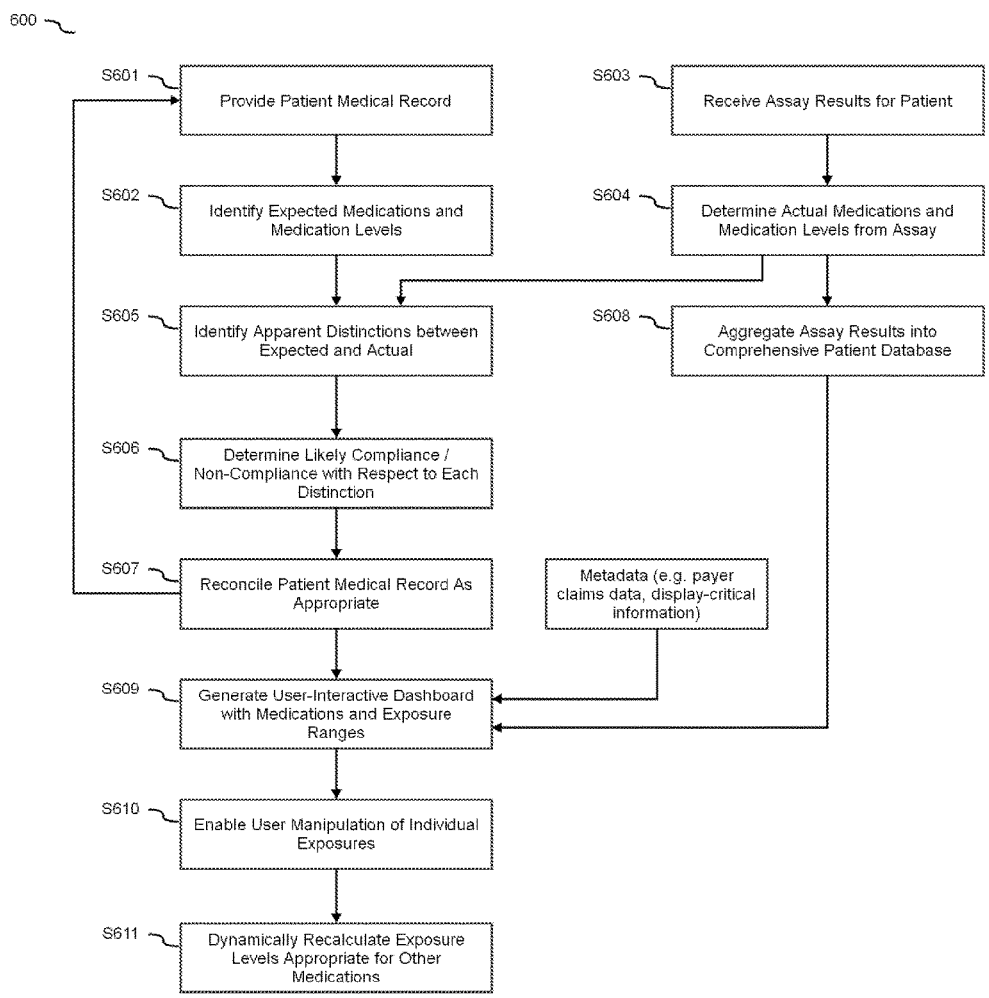
FIG. 6 is a flowchart representing an embodiment of a method for dynamically determining dosages in accordance with the present disclosure.

FIG. 6 is a flowchart representing another embodiment of a method for dynamically optimizing medication dosages in accordance with the present disclosure. The method 600 begins at a first step S601 wherein the system provides, receives or otherwise obtains access to a patient medical record. In an embodiment, the medical record may be obtained from an electronic medical records (EMR) database or a distributed medical record may be compiled via a network of databases in association with one or more healthcare providers. The patient medical record may contain medical information for the associated patient including, for example but in no way limited to, prescribed or otherwise expected medications. In step S602, the system identifies expected medications and associated medication exposure levels from the patient medical record. Expected medications and associated medication levels may include, for example, pharmaceutical prescriptions including the drug and dosage prescribed.

In step S603, the system receives the patient's assay results. In some embodiments as previously noted herein, the assay results may be determined from a patient fluid analysis, such as a blood analysis. In step S604, the system determines the "actual" or otherwise detected medications and medication exposure levels for the patient. In embodiments contemplating a blood analysis, the actual medications and medication levels may be associated with the actual medications and medication levels present within the patient's bloodstream at the time of the assay. Alternatively, the actual medications and medication levels may be associated with medications determined to be within the patient's bloodstream prior to the assay. For example, a medication with a known rate of excretion may be determined to have a comparatively higher medication level for the patient than the medication level measured at the time of the assay.

In step S605, the system identifies apparent distinctions between the expected medications and medication levels with the actual medications and medication levels. In an embodiment, the system may determine whether one or more medications are detected but not prescribed (unexpected), whether one or more medications are prescribed but not detected, and whether one or more medications are both detected and prescribed. In a further embodiment, the system may determine the degree of deviance between the actual medication levels and the expected medication levels for each of the determined medications.

In step S606, the system determines a likely compliance or non-compliance with respect to each distinction. For example, a medication both identified as expected and determined as actual may have a partial deviance between the expected and actual medication levels, the deviance being within or outside a range of tolerance for the medication, wherein the patient would be respectively determined in compliance or non-compliance for that medication. In a further embodiment, the range of tolerance for the determined medication may be determined from a plurality of factors including patient genetics, patient physiology, disease state, DDI with other determined medications, etc.

In other embodiments, the system may determine non-compliance where a medication is expected but not actual or actual but not expected.

In various embodiments, output data from the multiplex assay may for example be leveraged to produce a snapshot of patient compliance when medications are in the primary health record, but not detected in patient body fluids. For example, if both of parent drug and metabolic breakdown products are not detected via the assay results, and the pharmacokinetics determine that they should be detectable using known pharmacokinetic properties, non-compliance may be suspected. Alternatively, if only the parent drug or select metabolites are detected outside of known pharmacokinetic properties, inherent patient variability, such as genetic polymorphism presence, would be suspect, further triggering a variety of diagnostic or treatment options as may be available to the system and with respect to the relevant expected medication.

In an embodiment, genotypic analysis with respect to the patient, as well as relevant drug/metabolites can be used to distinguish between a non-compliant and high metabolizing patient. As but one illustrative example, if a parent drug fluoxetine was not detected by a healthcare provider in the relevant patient medication profile, and this medication was prescribed and indicated in the electronic health record, the healthcare provider may assume fluoxetine non-compliance. However, a small subset of patients contain multiple copies of the drug metabolizing enzyme CYP P450 2D6, and exhibit an ultra-rapid metabolizing phenotype of fluoxetine and other CYP 2D6-metabolized drugs. Measuring norfluoxetine in conjugation with fluoxetine by a host system as disclosed herein may alert the healthcare provider that this patient has an undetectable parent drug, high levels of the norfluoxetine metabolite, and is indeed compliant. Further, the recommended medication decision in this instance would not be for the healthcare provider to increase the fluoxetine dose, as this would be seemingly futile. Rather, in one embodiment the system may recommend this patient be switched to citalopram, which is not metabolized by the CYP 2D6 pathway, to achieve exposure levels in the patient necessary to treat depressive diagnosis. The hosted system may preferably track and continuously update its underlying informatics component with respect to these pharmacokinetic and all other pharmacogenomically-relevant polymorphisms that can be used to optimize pharmacotherapy.

In step S607, the patient medical record is reconciled to bring the patient medical record in line with at least the determined actual medications. As but one illustrative example, assay results may indicate that a patient is taking Warfarin but the patient medical record does not indicate that the patient was prescribed Warfarin, wherein the patient medical record may be updated with a Warfarin prescription. The Warfarin detected needs to be in the medical record such that physicians know the patient is on a potent blood thinner prior to performing a procedure (GI scope). Without reconciliation of the medical record, a physician would perform the procedure resulting in a GI bleed as complicated. Alternatively, with proper reconciliation, a subsequent iteration may therefore have less overall deviance and non-compliance for medications, absent variance between the first and second assay results.

Another example may include the same patient taking multiple antidepressants, wherein two are at dangerously high levels. Consultation would be necessary to reduce the dosage or remove one medication to avoid the risk of 'seretonin syndrome.'

The patient may further be non-compliant with their simvastatin, so that they are not adequately addressing the cardiovascular diagnosis of dyslipidemia from their cardiologist. Simvastatin needs to be taken, and this may be demonstrated adequately through appropriate reconciliation of the record with the determination of non-compliance.

Finally, the complications of adding simvastatin or adjusting paroxetine may change the potential for drug-drug interactions with this patient. The algorithms of the host system may preferably guide dose adjustments and medication switches relative to the patient's entire medication paradigm.

In an embodiment, the reconciliation may be made with the assistance of a healthcare provider consultation. For example, the unexpected presence or absence of a medication may indicate either a missing medical record entry for that medication or alternatively indicate that the patient is taking a medication not intended to be prescribed. Likewise, non-compliance for medication levels may indicate an improper prescription dosage or patient's improper following of dosage directions. Consultation with a healthcare provider may provide additional information for reconciling the patient medical record either to document intended medications missing from the medical record or to document unintended medications and advise the patient accordingly.

In an embodiment, output data from the multiplex assay may be analyzed relative to therapeutic class to illustrate non-intentional polypharmacy redundancy in treatment, which is common and increases proportionally to the number of prescribing physicians. Appropriate reconciliation of medication duplicity in the medical record, as determined in accordance with systems and methods of the present disclosure, may further alert healthcare providers in subsequent encounters or at least suggest medication switches relative to the patient's entire medication paradigm.

In step S608, the system aggregates the assay results into a comprehensive patient database. In an embodiment, the aggregation may be associated with the patient for subsequent display via a graphical user interface. In further embodiments, the aggregation may be statistically comparable to other assay results and assay result sets. For example, multiple assay results may be compared for one patient, for a group of patients, or for all patients in association with the patient database. Empirical data within the relational database can be used to re-define the therapeutic range of individual drugs when sufficient data are accumulated to be deemed superior to existing range estimates.

In an exemplary embodiment, further in view of previously disclosed embodiments, aggregation of assay results for the patient with assay results from each of a plurality of patients in a comprehensive patient database correlating medications and medication levels across a data model comprising one or more pharmacokinetic and pharmacodynamic dimensions. A host system and method as disclosed herein may accordingly leverage machine learning extrapolation from the comprehensive patient database for the purpose of determining exposure values for each of the expected medications (via, e.g., the medical records), the detected medications (via, e.g., analysis of assay results and patient metabolic characteristics), and associated exposure ranges.

In step S609, the system generates a user-interactive dashboard with displayed medications and exposure ranges for said medications for the associated patient. In an embodiment, the display may be configured for manipulation via a touchscreen interface, standard PC input/output such as mouse and keyboard, and the like. The system enables user manipulation of the individual exposures (step S610). In an embodiment, the user manipulation may be via the user-interactive dashboard. For example, a dashboard may display a plurality of medications and medication exposure levels which the user may add or subtract, and increase or decrease, respectively. In an embodiment, the system may make an initial calculation of exposure levels appropriate for the determined actual medications.

As the user manipulates individual exposures for each displayed medication, the system in step S611 dynamically recalculates the exposure levels as appropriate for other medications based at least upon relative DDI between the adjusted medication and other medications. For example, the increasing of the exposure of one medication may necessitate the reduction of another medication's exposure to decrease the risk of negative DDI, further requiring a change in dosage from the healthcare provider. In an alternative example, the increasing of one exposure may necessitate the increasing of another exposure to maintain efficacy. In a further example, the increase or decrease of a exposure may necessitate the discontinuation of another medication in the event of a negative DDI, wherein a substitute medication and exposure may be deemed appropriate to maintain efficacy while reducing negative DDI.

Figure 7:
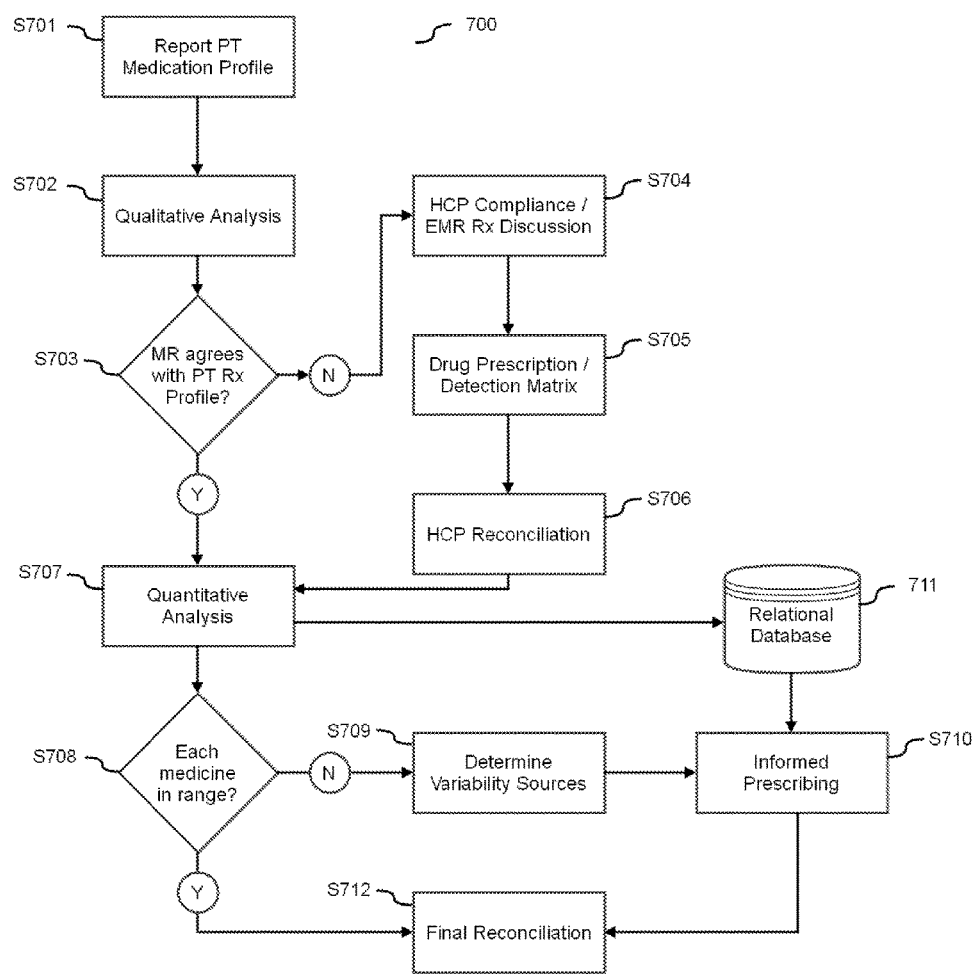
FIG. 7 is a flowchart representing a decision tree process for informed prescribing according to the present disclosure.

FIG. 7 is a flowchart representing a decision tree process for informed prescribing according to the present disclosure. In an embodiment, FIG. 7 may be interpreted as a concurrent process to method 600 of FIG. 6. The process 700 begins at a first step S501 by creating a patient medication profile. The profile may contain medications expected in accordance with data determined from the patient's medical record and medications determined in accordance with the assay results.

Upon generation of the report, the system initiates a qualitative analysis (step S702), wherein for each medicine a determination is made as to whether each medicine is prescribed as detected and detected as prescribed.

The system determines whether the patient's medical record agrees with the patient's medication profile (step S703). If the profile and records agree with one another, then the system moves on to step S707. If the profile and records do not agree with one another, then the system proceeds to step S704, wherein the patient-associated healthcare provider discusses with the patient the patient's adherence and the patient's medical record. In an embodiment, the healthcare provider may reconcile deviations between the medical record and patient adherence as either or both deficiencies regarding patient adherence and deficiencies regarding medical records.

The determination of medications that are detected but not prescribed and prescribed but not detected may be determined in accordance with a drug prescription-detection matrix (step S705), thereby identifying which medications are deviant from their expected results. For example, the system may generate a list of medications detected but not prescribed and a list of medications prescribed but not detected, thereby enabling the healthcare provider to question the patient about medication history and adherence.

The healthcare provider may then attempt to reconcile deficiencies (step S707), wherein patient adherence deficiencies are corrected through instruction of proper adherence and medical record deficiencies are reconciled with the addition or subtraction of deviant medications. For example, if the deviation is determined to be a patient adherence deficiency, the healthcare provider may be able to instruct the patient on the correct dosing procedures. Alternatively, if the deviation is not a patient adherence deficiency, the healthcare provider may indicate no deficiency, wherein the healthcare provider may elect to adjust the prescription if needed.

As another example, a medication detected but not prescribed may indicate a deficiency in the medical record. Healthcare provider inquiry with the patient may yield results as to whether the detected medication was validly prescribed. The healthcare provider may therefore determine that the medical record is deficient and may correct the record accordingly, or alternatively may determine that the detected medication is an adherence deficiency; for example, the patient may have accidentally swapped prescription bottles with a spouse.

Step S708 is a quantitative analysis phase, wherein the system determines for each medicine whether the dosage is within an initial reference range. The system first determines for each medicine whether the medicine is within the initial reference range based at least upon the patient medical record.

For example, a medication with a given prescription dosage as prescribed to the patient may have an initial reference range of 35 ng/mL to 350 ng/mL. If the medication as detected in the assay is below 35 ng/mL or above 350 ng/mL, then the medication would not be within the initial reference range, and if the medication as detected in the assay is at or between 35 ng/mL and 350 ng/mL, then the medication is within the initial reference range.

If each medication is within the initial reference range, then the system proceeds to step S712. If a medication is not within the initial reference range, then the system proceeds to step S709 to determine any variability sources for the errant medication. Variability sources may include DDIs, disease state, genetics, patient physiology, and the like. For example, the presence of another medication, the state of a treated disease, patient genetics, and patient physiology all may affect the metabolism or excretion of a given medication, which could cause deviation from an initial reference range. In an embodiment, one or more variability sources may have secondary reference ranges. In another embodiment, secondary reference ranges may be dynamically determined from the compilation of variability source data and effect data.

Upon determination of the variability sources, the system may engage in informed prescribing (step S710), wherein medication variability is adjusted to reconcile the medication profile for the patient. For example, a medication detected in a dosage lower than the reference range for that medication may result in a suggestion to increase the medication dosage or the medication titer. The informed prescription step may employ a relational database 711 storing medication interaction data. For example, the recommended adjustment of one medication may be determined from the relational database 711 to be problematic when combined with the presence of another medication, resulting in a negative DDI. The informed prescription may therefore recommend the substitution of one or more medications determined not to have problematic interactions and negative DDIs, thereby eliminating potential medication conflicts and normalizing medication exposure within each medication's reference range.

In step S712, the system performs a final reconciliation of prescription information based upon the changes performed within the step S711, if any, and empirical data as determined from historical relational and medication information. For example, the switching of one medication for another for a patient may have a predicted effect based upon the patient's physiology or genetics as determined from drug interaction data in association with the patient's particular physiological or genetic traits. More specifically, a chosen prescription may be deemed problematic based upon the patient's age. The drug interaction data may be determined from preprogrammed information such as pharmacy informatics and/or historical data as determined from previous iterations. For example, a prescription of gemfibrozil may generate an alert where a patient is co-administered with simvastatin for dylipidemia based upon pharmacy informatics because of a known lethal drug interaction; co-prescription of a beta-blocker may generate an alert where a patient's blood pressure is high and the patient has been prescribed Lisinopril based upon historical blood pressure data and Lisinopril prescription data for at least that patient.

The informed prescribing and final reconciliation may account for various levels of medication analysis. In an embodiment, the prescription and reconciliation may account for prescribing frequency, co-prescribing frequency, pharmacokinetics for determination of real-world DDIs, pharmacodynamics for determination of competitive and/or biologically redundant medications, and pharmacogenetics for determination of variable efficacy dependent upon human polymorphisms.

Figure 8A:
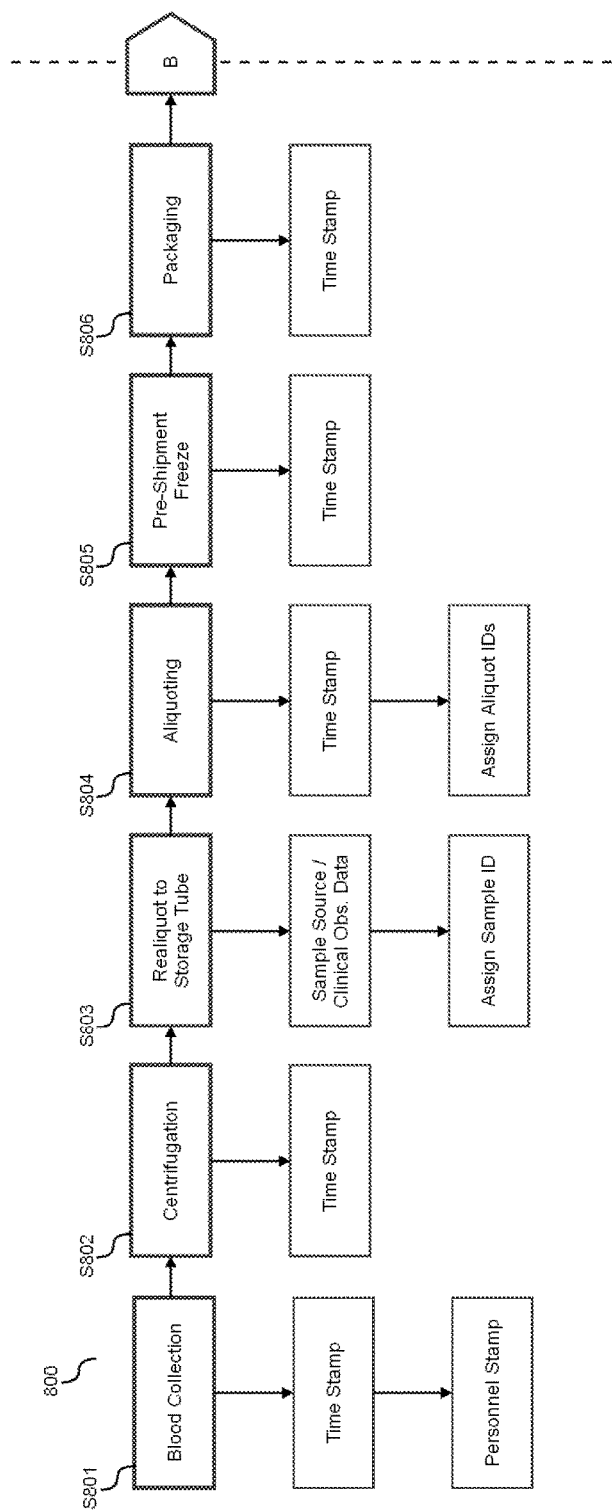
FIG. 8A is a flowchart demonstrating a first portion of a process for assay management and associated chain of custody requirements according to the present disclosure.
Figure 8B:
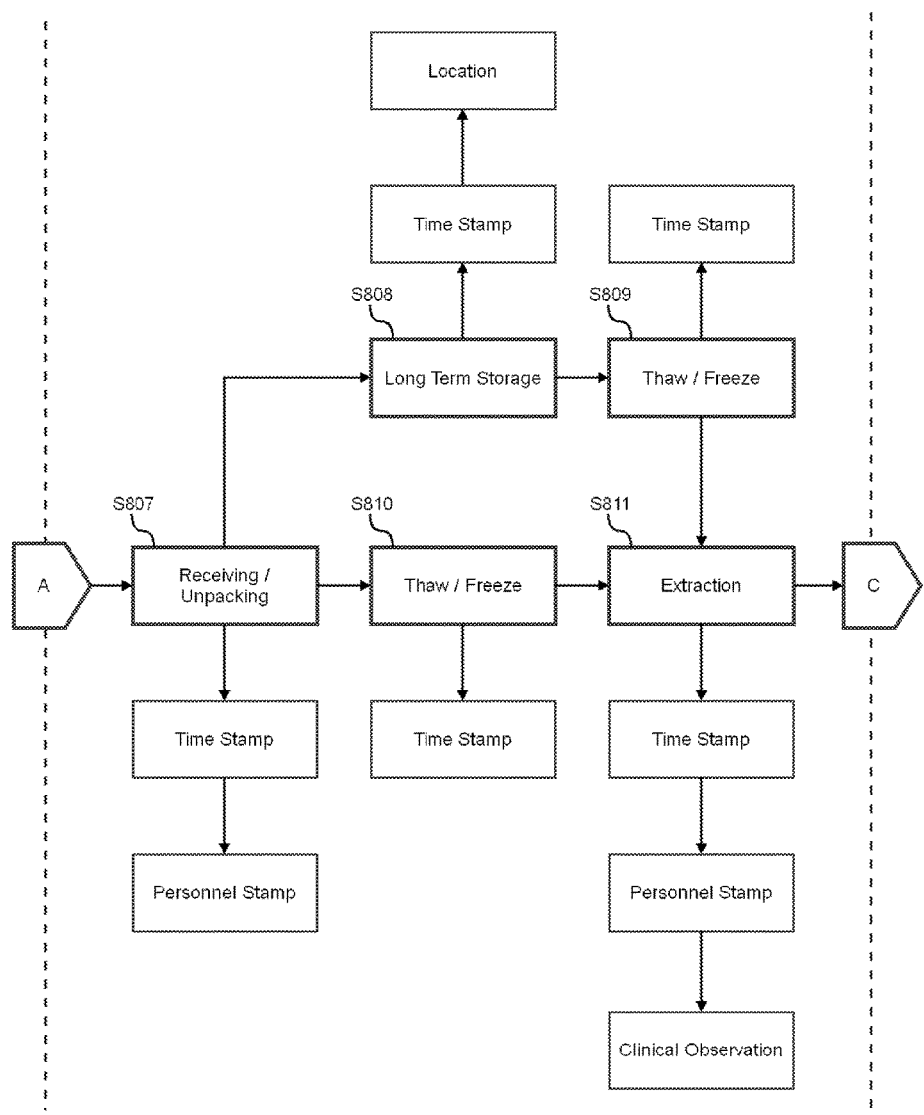
FIG. 8B is a flowchart demonstrating a second portion of the process in FIG. 8A.
Figure 8C:
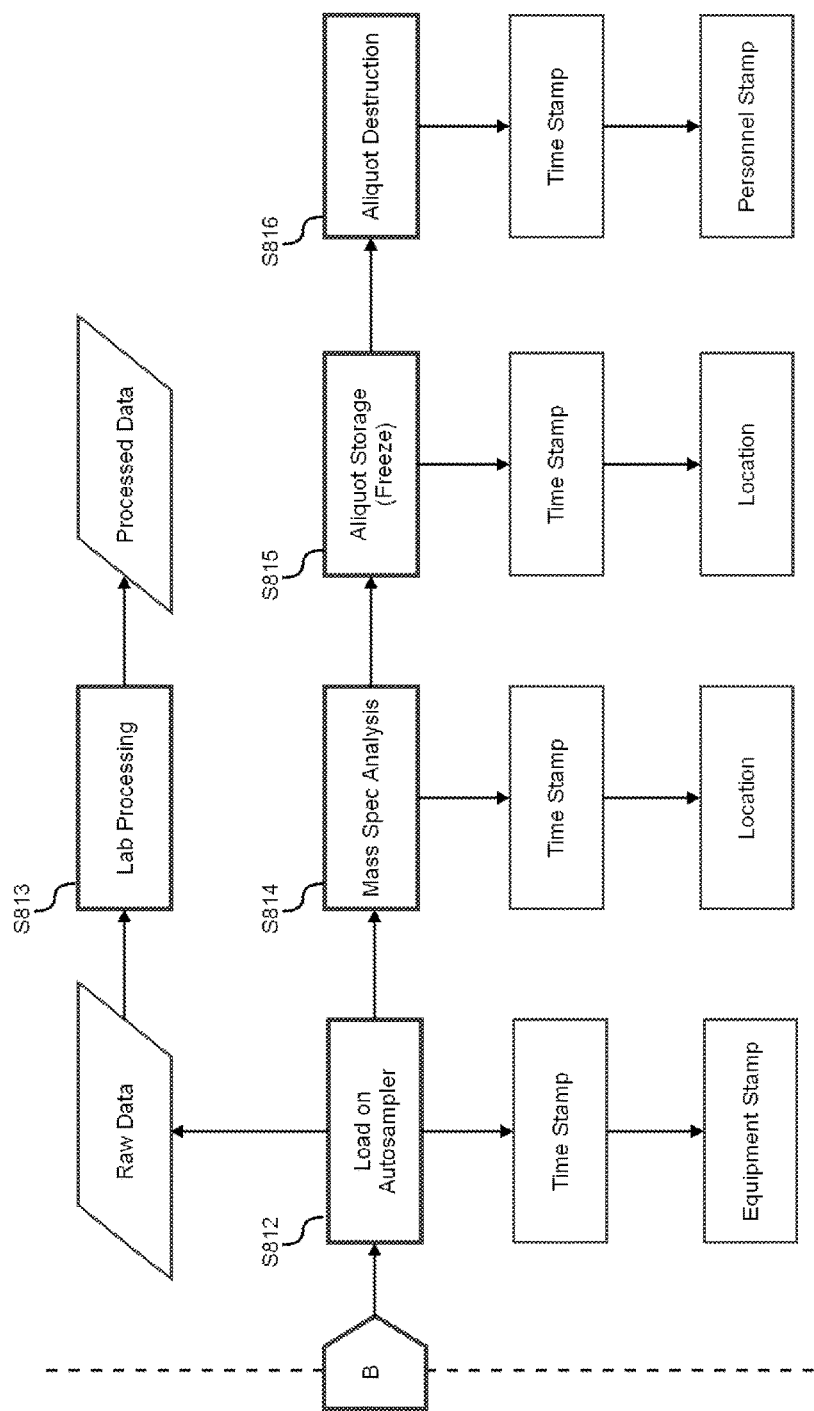
FIG. 8C is a flowchart demonstrating a third portion of the process in FIG. 8A.

FIGS. 8A-8C show a flowchart demonstrating a process for assay management and associated chain of custody requirements according to the present disclosure. The present embodiment contemplates a blood test. Each step of process 800 may be associated with one or more chain of custody steps to determine proper handling of the sample and assay procedures. Chain of custody steps may include steps such as requiring a time, equipment, and/or personnel stamp for a given procedure; assigning sample IDs; requiring clinical observation; recording location data; etc. a chain of custody record may in some embodiments be recorded in a central custody database.

The process 800 begins at a first step S801 wherein blood is drawn from a patient and collected, a time stamp and personnel stamp recorded for the drawn specimen. The blood specimen is sent for centrifugation and spun, whereupon a centrifugation time stamp is recorded (step S802). The separated blood specimen is then realiquoted to a storage tube and assigned a sample ID (step S803). The blood specimen is then aliquoted into samples, each assigned a time stamp and aliquot ID (step S804). The samples are then submitted to a pre-shipment freeze with an associated time stamp (step S805). The frozen samples are then packaged with a recorded packaging time stamp (step S806) for subsequent delivery.

Upon delivery, the samples are received and unpacked (step S807). In an embodiment, one or more blood samples may be sent to long term storage, wherein the frozen blood samples are recorded with a storage time stamp and storage location (step S808). Upon removal from storage the sample may be subsequently thawed with a thawing timestamp (step S809) and, if required, refrozen. For blood samples not sent to long term storage, the samples may be immediately thawed and, if necessary, refrozen (step S810). The sample may then be extracted, whereupon a time stamp, personnel stamp, and clinical observation procedural adherence is recorded (step S811).

The extracted sample is then loaded onto an autosampler, wherein a time stamp and equipment stamp in association with the time and specific autosampler device is recorded in association with the extracted sample (step S812). The autosampler extracts raw data, which is sent to a third-party laboratory for processing (step S813). The processed data may subsequently be used in association with the determination of assay results for a patient and actual medication and medication levels for said patient.

Further data may be determined in accordance with a mass spectrometry analysis of the sample, with associated time stamp and location information (step S814). The remaining aliquot may then be stored, optionally via freezing, wherein a time stamp and storage location is assigned (step S815). Upon expiration of the storage period, the aliquot may be destroyed, wherein the recorded destruction time and acting personnel is recorded (step S816).

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A decision support method for optimizing medication dosages, the method comprising:
    measuring for each of a comprehensive plurality of medications from respective body fluid samples for each of a plurality of patients, and identifying actual concomitant medication levels for any one or more actual medications associated with the patients as a subset of the comprehensive plurality of medications;
    iteratively developing proprietary drug interaction data in data storage over time, said drug interaction data based only on the identified concomitant medication levels and historical patient data for the respective patients comprising administered dosages of the one or more associated medications;
    identifying one or more expected medications and desired exposure values for a first patient of the plurality of patients from at least an associated patient medical record;
    determining one or more actual medications and exposure values for the patient from at least multiplex assay results associated with the patient;
    with respect to each of one or more distinctions between the expected and actual medications and exposure values, implementing analyses of patient genotype, and of medications and metabolites as determined from the assay results, to distinguish between a non-compliance state for the patient and a compliance state for the patient further in view of high metabolizing characteristics as masking actual exposure values for an associated medication;
    predicting potential medication levels corresponding to potential dosages for each identified expected medication and actual medication associated with the first patient based on at least the drug interaction data and the identified concomitant medication levels relative to the corresponding administered dosages;
    generating a recommended dosage for each of the one or more identified expected medications and actual medications based on a desired outcome and the respective predicted medication level;
    graphically generating a user interactive interface on a display unit comprising the recommended dosage values for each of the one or more identified expected medications and actual medications, and associated projected exposure ranges for each of the displayed medications;
    enabling user manipulation of respective dosage values for any one or more of the identified expected and actual medications; and
    dynamically calculating and displaying in real time projected exposure values for each of the one or more identified actual and expected medications based on the one or more user manipulated dosage values and on the drug interaction data.

2. The decision support method of claim 1, wherein exposure values are determined for each of the one or more identified expected medications, each of the one or more determined actual medications, and associated exposure ranges, based at least in part on machine learning extrapolation from the comprehensive patient database.

3. The decision support method of claim 2, wherein medication duplicity is determined for a plurality of identified expected medications.

4. The decision support method of claim 2, wherein non-compliance for an expected medication is determined upon failing to detect both parent medication and metabolic breakdown products, further wherein both of said parent medication and metabolic breakdown products are determined as detectable using associated pharmacokinetic properties.

5. The decision support method of claim 2, wherein upon detecting parent medication or metabolic breakdown products only outside of associated pharmacokinetic properties for an expected medication, further triggering presentation of one or more alternative treatment options with respect to the expected medication for display on the interactive user interface.

6. The decision support method of claim 5, further comprising:
    enabling user selection of one or more alternative treatment options for any of the expected medications; and
    dynamically calculating and displaying projected exposure values for each of the one or more medications based on the selected one or more alternative treatment options.

7. The decision support method of claim 1, wherein the user interactive interface for an exposure range associated with each of the one or more medications comprises a horizontally oriented display including a first value to a second value defining the projected exposure range,
    further wherein the enabled user manipulation comprises engaging and horizontally sliding an icon corresponding to a respective dosage value for one of the medications along the respective display.

8. The decision support method of claim 1, wherein the displayed projected exposure values for the one or more medications comprise recommended dosages for each of the respective one or more medications based on a drug interaction output and a measured effectiveness with respect to historical patient data.

9. A server system comprising:
    a processor,
    data storage comprising
        historical patient data for a first patient, comprising one or more expected chemical entities and desired exposure values,
        general chemical entity effectiveness data for each of a first plurality of chemical entities, corresponding to different historical outcomes resulting from variable medication levels in patients administered equivalent dosages of a given chemical entity, and
        drug interaction data iteratively developed over time from previously integrated data comprising medication levels and corresponding administered dosages, said drug interaction data corresponding to detected interactions for each of the first plurality of chemical entities with respect to one or more concomitantly administered chemical entities, said interactions detected only from the previously integrated data, a computer-readable medium having program instructions residing thereon, the processor configured to execute the program instructions and to direct the performance of operations further comprising:

measuring each of the first plurality of chemical entities in a multiplex format from a body fluid sample for the first patient and identifying a second plurality of actual chemical entities associated with the first patient as a subset of the first plurality of chemical entities;

identifying actual exposure values for each of the second plurality of measured chemical entities relative to respective target ranges, and relative to corresponding administered dosages retrievable from the historical patient data;

with respect to each of any one or more distinctions between the expected and actual chemical entities and exposure values, implementing analyses of patient genotype, and of medications and metabolites as determined from assay results, to distinguish between a non-compliance state for the patient and a compliance state for the patient further in view of high metabolizing characteristics as masking actual exposure values for an associated chemical entity;

iteratively integrating the identified exposure values and the corresponding administered dosages from the historical patient data to the drug interaction data in the data storage;

predicting exposure values for the first patient corresponding to potential dosages for each of the second plurality of chemical entities based on at least the drug interaction data and the identified exposure values relative to the corresponding administered dosages;

generating a recommended dosage for each of the second plurality of chemical entities based on a desired outcome and the respective predicted exposure value;

generating a user interface accessible via a display unit for a user computing device, the user interface comprising identified exposure values, the respective target ranges, and user-selectable visual elements corresponding to the respective recommended dosages for each of the second plurality of chemical entities associated with the patient;

in response to user selection and manipulation of a visual element for a first chemical entity from a first exposure value to a second exposure value, dynamically recalculating and displaying in real time one or more of the identified exposure value, target range and recommended dosage for each of the second plurality of chemical entities associated with the patient, based at least in part on the drug interaction data in the data storage and the identified or manipulated exposure values for each of the second plurality of chemical entities associated with the patient.

10. The server system of claim 9, wherein concomitant exposure values are used as covariates in generating recommended dosages for each of the second plurality of corresponding chemical entities.

11. The server system of claim 9, wherein non-compliance for an expected chemical entity is determined upon failing to detect both parent chemical entity and metabolic breakdown products, further wherein said chemical entity and metabolic breakdown products are determined as detectable using associated pharmacokinetic properties.

12. The server system of claim 11, wherein upon detecting parent medication or metabolic breakdown products only outside of associated pharmacokinetic properties for an expected chemical entity, further triggering presentation of one or more alternative treatment options with respect to the expected chemical entity for display on the interactive user interface.

13. The server system of claim 9, further comprising:
enabling user selection of one or more alternative treatment options for any of the expected chemical entities; and
dynamically calculating and displaying projected exposure values for each of the one or more chemical entities based on the selected one or more alternative treatment options.

14. The server system of claim 9, wherein the user interactive interface for an exposure range associated with each of the one or more chemical entities comprises a horizontally oriented display including a first value to a second value defining the projected exposure range,
further wherein the enabled user manipulation comprises engaging and horizontally sliding an icon corresponding to a respective dosage value for one of the chemical entities along the respective display.

15. The server system of claim 9, wherein the displayed projected exposure values for the one or more chemical entities comprise recommended dosages for each of the respective one or more chemical entities based on a drug interaction output and a measured effectiveness with respect to historical patient data.

* * * * *